(12) United States Patent
Nie et al.

(10) Patent No.: US 7,816,321 B2
(45) Date of Patent: Oct. 19, 2010

(54) THYMOSIN β4 DERIVATIVES AND USE THEREOF (75) Inventors: Liya Nie, Beijing (CN); Suyong Ma, Beijing (CN); Songshan Xu, Beijing (CN); Meiyu Wen, Beijing (CN)

(73) Assignee: Beijing Northland Biotech. Co., Ltd., Beijing (CN)

(*) Notice: Subject to any disclaimer, the term of this patent is extended or adjusted under 35 U.S.C. 154(b) by 38 days.

(21) Appl. No.: 11/995,817

(22) PCT Filed: Jul. 14, 2006

(86) PCT No.: PCT/CN2006/001679

§ 371 (c)(1),
(2), (4) Date: Aug. 20, 2008

(87) PCT Pub. No.: WO2007/009359

PCT Pub. Date: Jan. 25, 2007

(65) Prior Publication Data

US 2009/0298758 A1    Dec. 3, 2009

(30) Foreign Application Priority Data

Jul. 15, 2005  (CN) .......................... 2005 1 0083894
Sep. 23, 2005  (CN) .......................... 2005 1 0103293

(51) Int. Cl.
*A61K 38/22*    (2006.01)
*C07K 14/575*   (2006.01)
*C12N 15/11*    (2006.01)

(52) U.S. Cl. ........................................ 514/12; 530/399
(58) Field of Classification Search .................. None
See application file for complete search history.

(56) References Cited

U.S. PATENT DOCUMENTS 4,297,276 A    10/1981   Goldstein et al. ...... 260/112.5 R
4,395,404 A    7/1983    Low et al. ................ 424/177

FOREIGN PATENT DOCUMENTS

WO    WO 0006190        *  2/2000
WO    2006126102 A2        11/2006

OTHER PUBLICATIONS

Huff, 2001, the international Journal of Biochemistry and Cell Biology, vol. 33, 205-220.*
Abiko, 1990, Chemical Pharmaceutical Bulletin, vol. 38, Issue 9, pp. 2602-2605.*
Rossenu, Stefaan et al, "A Phage Display-based Method for Determination of Relative Affinities of Mutants," *J. Biol. Chem.*, 278(19):16642-50, May 9, 2003.
Simenel, Catherine et al., "Structural Requirements for Thymosin β4 in its Contact with Actin. An NMR-Analysis of Thymosin β4 Mutants in Solution and Correlation with their Biological Activity," *Eur. J. Biochem.*, 267:3530-38, Jun. 2000.
Goldstein et al., "Thymosin β4: actin-sequestering protein moonlights to repair injured tissues" Trends in Molecular Medicine 11(9): 421-429, Sep. 2005.
Nie et al., "Expression of thymosin beta 4 mRNA expression in keloid tissues and fibroblasts cultured from keloid and its significance" Zhongguo Wei Zhong Bing Ji Jiu Yi Xue 17(2): 80-83, Feb. 2005 (English Abstract, 1 page.).
Mammalian Gene Collection (MGC) Program Team, "Generation and initial analysis of more than 15,000 full-length human and mouse cDNA sequences" Proc. Natl. Acad. Sci. 99(26): 16899-16903, Dec. 24, 2002.
Supplemental International Search Report, mailed Sep. 15, 2009, for PCT/CN2006/001679, 8 pages.

* cited by examiner

*Primary Examiner*—Robert Landsman
*Assistant Examiner*—Ian Dang
(74) *Attorney, Agent, or Firm*—Seed IP Law Group PLLC (57) ABSTRACT

The present invention relates to thymosin β4 (Tβ4) derivatives, Gly-Tβ4 and Ala-Tβ4. The present invention further relates to a pharmaceutical composition comprising the said Tβ4 derivatives. The present invention also relates to the use of said Tβ4 derivatives in manufacture of a medicament for treatment of skin lesion, heart injury, corneal lesion and/or coronary heart disease. The present invention further relates to a method of treatment for skin lesion, heart injury, corneal lesion and/or coronary heart disease by using the said Tβ4 derivatives.

4 Claims, 6 Drawing Sheets

Fig.9A      PBS group, on the 1st day after treatment

Fig.9B      Ala-Tβ4 group, on the 1st day after treatment

Fig.9C      Tβ4 group, on the 1st day after treatment

Fig.10A          PBS group, on the 5ˢᵗ day after treatment

Fig.10B          Tβ4 group, on the 5ˢᵗ day after treatment

Fig.10C          Ala—Tβ4 group, on the 5ˢᵗ day after treatment

THYMOSIN β4 DERIVATIVES AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 140162_401 USPC_SEQUENCE_LISTING.txt. The text file is 3.4 KB, was created on Jun. 9, 2009, and is being submitted electronically via EFS-Web.

TECHNICAL FIELD

The present invention relates to thymosin β4 (Tβ4) derivatives, Gly-Tβ4 and Ala-Tβ4. The present invention further relates to a pharmaceutical composition comprising the said Tβ4 derivatives. The present invention also relates to the use of said Tβ4 derivatives in manufacture of a medicament for treatment of skin lesion, heart injury, corneal lesion and/or coronary heart disease. The present invention further relates to a method of treatment for skin lesion, heart injury, corneal lesion and/or coronary heart disease by using the said Tβ4 derivatives.

BACKGROUND ART

Immune system is a defense system of human body. The main cells involving a immune response are T lymphocytes, B lymphocytes, and macrophages. Thoracic gland is the central immune organ for development and differentiation of T lymphocytes. Thymus factors (or hormones) secreted from thoracic gland are a series of essential substances necessary for development and differentiation of T lymphocytes, wherein Tβ4 is one of main thymus factors which structure and functions are relatively definite and known in the art. It is well known in the art that, Tβ4 was a polypeptide that firstly isolated by Goldstein, et al., from thymosin fraction 5 (TF5) extracted from bovine thoracic gland with 43 amino acids as shown in SEQ ID NO: 1, had a molecular weight of 4.963 KD, was free of disulfide bond and glycosylation (The Journal of Biological Chemistry, Vol. 257, No. 2, pp. 1000-1006, 1982, Chemical Characterization of Thymosin beta).

Tβ-4 is a protein expressed during the onset of heart disease in embryo, and is able to promote the migration of cardiac cells and influence the survival of these cells (Thymosin beta 4 activates integrin-linked kinase and promotes cardiac cell migration, survival and cardiac repair. Nature, Vol. 432, Nov. 25, 2004). As indicated in the above document, said protein was able to prevent cells from death and to limit the formation of scare tissue in some extent after the onset of experimentally induced heart disease. Tβ-4 has been applied in clinical trials to promote the healing of skin wound. Researchers believe that Tβ-4 will be used in clinical trial phase for treatment of heart diseases in the near future.

As shown in one of the aforementioned researches on Tβ4 activity, Tβ4 improved the survival of embryonic and post-natal myocardial cells in tissue culture, and intra-peritoneal injection of said protein after deligation of coronary artery in rats could successfully stimulate heart repair and activate Akt survival kinase. These results indicated that T-β4 is a potential therapeutic target for acute coronary artery occlusion.

In the above documents, the researchers of State University of Texas also found a protein (i.e., Tβ4) produced during the development of heart could facilitate heart self-repairing after the onset of heart disease. The findings obtained in rat might finally result in the discovery of new methods for treatment of heart diseases and could change the treatment of heart diseases in the art.

New Tβ-4 derivatives having significantly higher activity than that of native Tβ-4 regarding repair of skin lesion, heart injury, etc. is unexpectedly found by the inventors of the present invention by taking tertiary structure analysis of the known Tβ-4, and genetic engineering modification of the N-terminal of the said protein.

SUMMARY OF THE INVENTION

One aspect of the present invention relates to a new Tβ4 derivative, which is Gly-Tβ4 as shown in SEQ ID NO:6 and Ala-Tβ4 as shown in SEQ ID NO:5, respectively.

It is well known in the art that the said Gly-Tβ4 and Ala-Tβ4 can be expressed by a method of genetic recombination or prepared by a method of chemical synthesis. In the present invention, the said Gly-Tβ4 and Ala-Tβ4 are obtained by a method of recombination and expression via genetic engineering.

In one embodiment of the present invention, a thymosin β4 derivative with modified N-terminal, i.e., Gly-Tβ4 or Ala-Tβ4, is obtained by a method comprising the following steps:

1) Construction of Expression Vector

According to the known amino acid sequence of Tβ4 (SEQ ID NO: 1), the DNA sequence of Tβ4 is synthesized de novo by using preferential codon of *E. coli* with addition of restriction sites corresponding to the N-terminal and C-terminal of the amino acid sequence encoded thereby, and modification of its N-terminal, and thereby a nucleic acid sequence encoding a Tβ4 derivative, Gly-Tβ4 or Ala-Tβ4 is obtained. According to the known amino acid sequence of GST, a leader peptide DNA sequence is synthesized de novo by using preferential codon of *E. coli* with addition of restriction sites corresponding to the N-terminal and C-terminal of the amino acid sequence it encoded, and a leader peptide nucleic acid sequence is obtained thereby.

The sequence of leader peptide and Tβ4 derivative prepared as above and a screening plasmid pBSK are treated with restriction enzyme, and added into a T4 ligation system in certain molar ratio as calculated according to the concentrations of component. The desired recombinants are screened out via transformation.

Gene of fusion protein is digested by using restricted enzyme, then the gene is ligated to the plasmid pGM that has been treated with restricted enzyme (the plasmid pGM harboring a marker of kanamycin resistance can express GST fusion protein in large quantity, and is constructed by Beijing Northland Biotech Co., Ltd.), and the desired recombinant is obtained by screening.

2) Expression of Recombinant Tβ4 Derivative and Separation and Purification Thereof.

The above obtained recon is transformed into a bacteria expression host; after expression, high expression genetically engineered bacteria are screened out; and then the engineered bacteria with high expression of the desired protein are obtained by fermentation. The bacteria are broken by a high-pressure homogenizer and centrifuged to obtain a supernatant containing the desired precursor protein, the supernatant is loaded to a GST affinity column, the desired precursor protein is eluted and then digested by using thrombin, the resulted sample is further purified by applying to an anion column to obtain a final product with a protein purity of greater than 98%.

Another aspect of the present invention relates to a pharmaceutical composition, which comprises a Tβ4 derivative according to the present invention, Gly-Tβ4 and/or Ala-Tβ4, and optionally a pharmaceutically acceptable carrier.

In the present invention, the term "pharmaceutically acceptable" means generally recognized for use in animals, and more particularly in humans. The term "carrier" refers to a diluent, adjuvant (e.g., Freund's adjuvant (complete and incomplete)), excipient, or vehicle with which the therapeutic is contained in or administered.

Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

In one embodiment of the present invention, the said pharmaceutical composition is a lyophilized injectable form, which comprises 0.01%-0.2% thymosin derivative Gly-Tβ4 or Ala-Tβ4, 5% mannitol, and a pharmaceutically acceptable carrier.

The pharmaceutical composition of the present invention is formulated in a form compatible with the desired administration route. The examples of administration routes include but are not limited to parenteral administration, such as intravenous, intracutaneous, subcutaneous, oral, intranasal (such as inhale), percutaneous (such as topical), per mucomembranous and per rectal administration. In one specific embodiment, the composition is formulated to form a pharmaceutical composition suitable for intravenous, subcutaneous, intramuscular, oral, nasal or topical administration. Usually, the composition suitable for intravenous administration is a solution in a sterile isotonic aqueous buffer. If necessary, the composition further comprises solubilizing agent and topical anesthetic such as ergotamine in order to reduce pain at injection site.

In an embodiment of the invention, the said composition is a solution of eyedrop, comprising 50-500 μg/ml thymosin derivative Gly-Tβ4 and/or Ala-Tβ4, an antibiotic selected from the group consisting of chloromycetin or ofloxacin, and a pharmaceutically acceptable carrier. In another embodiment of the present invention, the said composition is a solution of eyedrop, comprising 50-500 μg/ml thymosin derivative Gly-Tβ4 and/or Ala-Tβ4, a suitable amount of sodium hyaluronate, and a pharmaceutically acceptable carrier. In another embodiment of the present invention, the said composition is a solution of eyedrop, comprising 50-500 μg/ml thymosin derivative Gly-Tβ4 and/or Ala-Tβ4, an amount of sodium hyaluronate, chloromycetin or ofloxacin, and a pharmaceutically acceptable carrier.

If the composition of the present invention is administrated topically, the composition can be formulated as ointment, cream, dermal patch, lotion, gel, shampoo, spraying agent, aerosol, solution, emulsion, or other forms well known by those skilled in the art (see also, Remington's Pharmaceutical Sciences and Introduction to Pharmaceutical Dosage Forms, 19$^{th}$ Edition, Mack Publishers, Easton, Pa., 1995).

As for topical dosage forms other than spraying agent, viscous to semisolid or solid forms are usually adopted which comprise a carrier or one or more excipients compatible with topical application and have a dynamic viscosity greater than that of water. Suitable formulations comprise but are not limited to solution, suspension, emulsion, cream, powder, varnish, ointment and so on, if necessary, are sterile or mixed with auxiliary agents (such as preservative, stabilizing agent, wetting agent, buffer or salt) to change their properties, such as osmotic pressure. Other suitable topical dosage forms comprise aerosols, wherein a solid phase or liquid phase carrier in combination with an active component are preferably packaged in a mixture or squeezable bottle containing a pressure volatile (such as compressed gas, such as Freon). If necessary, humidifier or moistening agent can be added in the pharmaceutical composition and dosage forms. The examples of these additional components are well known in the art.

In another embodiment of the present invention, the said pharmaceutical composition is an ointment, which comprises 0.01%-0.2% thymosin derivative Gly-Tβ4 and/or Ala-Tβ4, and a pharmaceutically acceptable excipient such as vaseline.

If the method of the present invention comprises the nasal administration of composition, the composition can be formulated in forms of aerosol, spraying agent, mist agent, or drop. Specifically, the prophylactic or therapeutic agent used in the present invention can be conveniently delivered in aerosol form by a pressure package or atomizer using a suitable propellant (such as dichlorodifluoromethane, trichlorofluoromethane, dichlorotetrafluoroethane, carbon dioxide, or other suitable gases). In the case of pressure aerosol, a dosage unit can be determined by providing a valve to deliver a measured amount. Inhalator or capsule and cartridge (for example, constituted with gelatin) used in inhalator can be formulated to contain a mixture powder comprising a compound and a suitable powdery matrix such as lactose or starch.

In further another embodiment of the present invention, the said pharmaceutical composition is a spraying agent, which comprises 5-500 μg/ml thymosin derivative Gly-Tβ4 or Ala-Tβ4, 0.003% ethyl p-hydroxybenzoate, and a pharmaceutically acceptable carrier.

If the method of the present invention comprises oral administration, the composition can be formulated in forms such as tablet, capsule, kit, soft capsule, solution, suspension, etc. The tablet or capsule can be formed by using conventionally pharmaceutically acceptable excipients, such as binding agents (such as pregelatinized starch, polyvinylpyrrolidone, or hydroxypropylmethylcellulose); filling agents (such as lactose, microcrystalline cellulose, or calcium hydrogen phosphate); lubricants (such as magnesium stearate, talc, or silica); disintegrants (such as potato starch or Explotab); or moistening agent (such as sodium sodium laurylsulfate). Tablets can be coated by methods well known in the art. Liquid preparations suitable for oral administration can be, but not limited to, a form of solution, syrup, or suspension, or in a dry form thereof that can be dissolved by water of other suitable solvent before administration. These liquid preparations can be prepared by conventional methods using pharmaceutically acceptable additives, such as suspending agents (such as sorbitol syrup, cellulose derivatives, or hydrogenated edible fats); emulsifying agents (such as lecithin, or Arabic gum); nonaqueous media (such as almond oil, oily esters, ethanol, or fractional vegetable oil); and preservatives (such as methyl or propyl p-hydroxybenzoate or sorbic acid). These preparations may further comprise buffer salts, flavoring agents, coloring agent, and sweeting agent. Preparations for oral administration can be appropriately formulated to form sustained release, controlled release, or continuous release prophylactic or therapeutic agent.

The method of the present invention further comprises formulating a composition for parenteral administration by injection (such as push injection or continuous transfusion). The preparation for injection can be a unit dosage form (such as in ampoule or multiple-unit container) comprising additional preservative. The composition can be in forms such as suspension, solution or emulsion in oily or oleaginous or aqueous media, and can comprise auxiliary agents such as suspending agent, stabilizing agent and/or dispersing agent. Or, the active component can be in powdery form and dissolved with suitable media (such as sterile, nonpyrogenic water).

The media suitable for the parenteral dosage forms of the present invention are well known by those skilled in the art. In some embodiments, the media suitable for the parenteral dosage forms include but are not limited to water for injection USP; the aqueous media include but are not limited to sodium chloride injection, Ringer's injection, glucose injection, glucose and sodium chloride injection, and lactic acid Ringer's injection; water miscible media include but are not limited to corn oil, cotton seed oil, peanut oil, sesame oil, ethyl oleate, iso-propyl myristate, and methyl benzoate.

The further another aspect of the present invention relates to the use of a Tβ4 with N-terminal modification selected from the group consisting of Gly-Tβ4 and Ala-Tβ4 in manufacture of a medicament for treatment of heart injury, skin lesion, corneal lesion and/or coronary heart disease.

The present inventor surprisingly found, in experimental on model animal, that the Gly-Tβ4 and Ala-Tβ4 of the present invention exhibited higher activity than native Tβ4 in terms of repair of injured heart tissue, repair of skin lesion, and repair of corneal lesion.

The effects of Gly-Tβ4 and Ala-Tβ4 on repair of heart tissue were assayed by the present inventor. 60 adult rats were subjected to coronary artery deligation to imitate the onset of heart disease and to obtain rat models with left anterior descending branch coronary artery ligation and reperfusion. Limited cells died in the injured rat heart with continuous injection of thymosin derivative Gly-Tβ4 or Ala-Tβ4 or thymosin Tβ4 for one month, and the heart functions were improved several weeks after the onset of heart disease, and the therapeutic effects of Gly-Tβ4 or Ala-Tβ4 were more significant than that of Tβ4. The present inventors found that thymosin derivative Gly-Tβ4 or Ala-Tβ4 could both change the metabolism of cells and create more powerful myocardial cells that resistant to low-oxygen condition after the onset of heart disease.

The effects of Gly-Tβ4 and Ala-Tβ4 on injured epidermal tissues were also assayed by the present inventor. 30 adult rats were cut on their epidermis to obtain rat epidermis lesion model. The length of wounds of rats which were smeared with thymosin Gly-Tβ4, Ala-Tβ4 or Tβ4 for 5 days were 50% smaller than the blank control, and the therapeutic effects of Gly-Tβ4 and Ala-Tβ4 were more significant than that of Tβ4.

The effects of Gly-Tβ4 on injured corneal tissue were also assayed by the present inventor. The corneas of 30 adult rats were burned with 1N NaOH to obtain rat corneal lesion models. The injured corneas of rats in which eyes thymosin Gly-Tβ4 or Tβ4 was dropped for 4 days were recovered completely, while the injured corneas of rats in the group treated with physiological saline not only were not recovered, but also suffered with severe inflammation and hyperemia.

The above results indicated that the Tβ4 derivative Gly-Tβ4 and/or Ala-Tβ4 of the present invention exhibited significantly higher activity than native Tβ4 in terms of treatment of heart tissue injury, epidermal tissue injury and corneal tissue injury. The further another aspect of the present invention relates to a method of using the said Tβ4 derivative Gly-Tβ4 and/or Ala-Tβ4 for treatment of heart tissue injury, epidermal tissue injury and corneal tissue injury of a subject, especially a human being. In one embodiment of the present invention, the method for treatment of heart tissue injury, epidermal tissue injury and corneal tissue injury comprises administering a therapeutically effective amount of the said Tβ4 derivative Gly-Tβ4 and/or Ala-Tβ4 of the present invention to the subject.

It is well known in the art that the manner, frequency and dosage for the administration depend on disease, condition of disease and individual. In general, the administration can be injection (intracutaneous, intramuscular, intravenous or subcutaneous injection), topical administration (such as epidermal administration) or dropwise administration (such as eyedrops). A suitable administration route and administration schedule could be selected dependent on the individual subject. Suitable dosage is an amount of the said pharmaceutical composition that can effectively treat heart tissue injury, epidermal tissue injury and corneal tissue injury after the administration thereof.

In general, as for a pharmaceutical composition which comprises the said Tβ4 derivative Gly-Tβ4 and/or Ala-Tβ4 of the present invention, the amount in each dose is about 100 μg-5 mg. Suitable dose depends on disease of patient and administration manner, but usually is about 0.1 ml-5 ml.

In accordance with Budapest Treaty on the International Recognition of the Deposit of Microorganisms for the Purposes of patent Procedure, the inventor deposited the recombinant strains PGMT β4-A/BL21 and PGMT β4-G/BL21 in China General Microbiological Culture Collection Center (CGMCC, Beiyitiao, Zhongguancun, Beijing, China) with access number CGMCC 1750 and CGMCC 1751, separately.

The present invention is further illustrated in conjugation with the drawings and examples, but is not restricted thereby.

EXAMPLE 1

Preparation of Thymosin β4 Derivative Gly-Tβ4

1. Preparation of Recombinant Plasmid pGMTβ4-G

In accordance with the known amino acid sequence of Tβ4 (SEQ ID NO:1),

```
Ser Asp Lys Pro Asp Met Ala Glu Ile    (SEQ ID NO:1)
Glu Lys Phe Asp Lys Ser Lys Leu Lys
Lys Thr Glu Thr Gln Glu Lys Asn Pro
Leu Pro Ser Lys Glu Thr Ile Glu Gln
Glu Lys Gln Ala Gly Glu Ser;
``` the DNA sequence of Tβ4 was synthesized de novo by using preferential codon of *E. coli*. To facilitate manipulation of gene recombination, restriction sites BamH I and Xho I, corresponding to the N-terminal and C-terminal of the peptide encoded thereby were added, and the N-terminal is modified with glycine, Gly, as shown in SEQ ID NO:2,

```
GGA TCC GAC AAA CCC GAT ATG GCT GAG    (SEQ ID NO:2)
BamHI
ATC GAG AAA TTC GAT AAG TCG AAA CTG
AAG AAG ACA GAG ACG CAA GAG AAA AAT
CCA CTG CCT TCC AAA GAA ACG ATT GAA
CAG GAG AAG CAA GCA GGC GAA TCG TAA
CTC GAG;
   XhoI
``` wherein, the restriction sites were underlined.

The corresponding amino acid sequence is as follows:

```
Gly Ser Asp Lys Pro Asp Met Ala Glu    (SEQ ID NO:6)
Ile Glu Lys Phe Asp Lys Ser Lys Leu
Lys Lys Thr Glu Thr Gln Glu Lys Asn
Pro Leu Pro Ser Lys Glu Thr Ile Glu
Gln Glu Lys Gln Ala Gly Glu Ser;
```

According to the known GST amino acid sequence, a leader peptide DNA sequence was synthesized de novo by using *E. coli* preferential codon, and restriction sites EcoRI and BamHI were added at sites corresponding to the N-terminal and C-terminal of the sequence, thereby obtaining a nucleic acid sequence of said leader peptide, as shown in SEQ ID NO:3:

```
GAATTCATGTCCCCTATACTAGGTTATTGGAAAATT    (SEQ ID NO:3)
EcoRI
```

```
AAGGGCCTTGTGCAACCCACTCGACTTCTTTTGGAA
TATCTTGAAGAAAAATATGAAGAGCATTTGTATCAG
CGCGATGAAGCTGATAAATGGCGAAACAAAAGTTT
GAATTGGGTTTGGAGTTTCCCAATCTTCCTTATTAT
ATTGATGGTGATGTTAAATTAACACAGTCTATGGCC
ATCATACGTTATATAGCTGACAAGCACAACATGTTG
GGTGGTTGTCCAAAAGAGCGTGCAGAGATTTCAATG
CTTGAAGGAGCGGTTTTGGATATTAGATACGGTGTT
TCGAGAATTGCATATAGTAAAGACTTTGAAACTCTC
AAAGTTGATTTTCTTAGCAAGCTACCTGAAATGCTG
AAAATGTTCGAAGATCCTTTATGTCATAAAACATAT
TTAAATGGTGATCATGTAACCCATCCTGACTTCATG
TTGTATGACGCTCTTGATGTTGTTTTATACATGGAC
CCAATGTGCCTGGATGCGTTCCCAAAATTAGTTTGT
TTTAAAAAACGTATTGAAGCTATCCCACAAATTGAT
AAGTACTTGAAATCCAGCAAGTATATAGCATGGCCT
TTGCAGGGCTGGCAAGCCACGTTTGGTGGTGGCGAC
CATCCTCCAAAATCGGATCTGGTTCCGCGTGGATCC;
                                 BamHI
```

According to conventional methods in the art (see also, "Molecular Cloning: A Laboratory Manual", 2$^{nd}$ Edition, Cold Spring Harbor Laboratory Press America, 1992), the above prepared leader peptide, Gly-Tβ4 and screening plasmid pBSK (Stratagene, #212205) were digested with restriction enzymes EcoRI, XhoI, BamHI, wherein EcoRI and BamHI were used to digest the lead peptide, XhoI and BamHI were used to digest Gly-Tβ4, and EcoRI and XhoI were used to digest the screening plasmid pBSK, wherein after calculation of concentrations of each components, they were added in a molar ratio of 1:1 into a T4 ligation system. After transforming and screening, a recombinant plasmid comprising the gene of said Gly-Tβ4 nucleic acid sequence and the leader peptide fusion protein was obtained and named as pSK-Tβ4.

The said fusion protein gene was digested by corresponding restriction enzymes separately, and then the fusion protein gene fragment and the recovered large fragment of plasmid pGM obtained by double enzyme digestion with XhoI and EcoRI (the plasmid pGM harboring a marker for kanamycin resistance screen, could express GST fusion protein in large quantity, and was constructed by Beijing Northland Biotech Co., Ltd.) were subjected to a ligation of three desired gene fragments in a T4 ligase system at 18° C. The obtained recons were identified by digesting and sequencing to obtain a recombinant plasmid with correct linkage, named as pGM Tβ4-G.

2. Preparation of Genetically Engineered Bacteria Harboring the Recombinant Plasmid pGMTβ4-G Then, *E. coli* BL21 was transformed in accordance with CaCl$_2$ method and spread on LB plate containing 50 μg/ml kanamycin, and positive colonies were chosen for identifying a transformant containing the said recombinant plasmid pGMTβ4-G.

The said transformant was cultured in LK liquid medium until OD$_{600}$ was 0.6-0.8, 0.1 mM IPTG was added for the induction of 3-4 hours before the bacteria were collected by centrifugation, then broken with 8M urea, one protein band of about 30 KD in 15% SDS-PAGE electrophoresis was shown with an expression level of 40%. The immunoblot assay of Tβ4 monoclonal antibody exhibited positive reaction. The obtained genetically engineered strain with high expression of thymosin derivative Gly-Tβ4 protein was named as PGM2Tβ4/BL21.

According to the above preparation method, a genetically engineered strain with high expression of thymosin derivative Gly-Tβ4 obtained by the applicant was named as PGMT β4-G/BL21 (access number of deposit: CGMCC No.1751).

3. Expression and Purification of Gly-Tβ4
  1) Expression in shake flask: the genetically engineered strain PGMT β4-G/BL21 as above prepared was cultured overnight in LB medium comprising 50 μg/ml kanamycin (37° C., 200 rmp), then was inoculated in a volume ratio of 1:30 into a LB medium comprising 50 μg/ml kanamycin, and cultured at 37° C. for 3 hours, then was induced for 4 hours by adding 0.1 mM IPTG. Cells were collected and analyzed by SDS-PAGE electrophoresis, and it was found that the thymosin derivative Gly-Tβ4 (30 KD) was mainly in form of soluble expression product, and the quantity of the expression product was 60% based on the total protein.
  2) Large scale fermentation and expression
    A. Composition of culture media
      a) Seed liquid medium (LK):
        Tryptone: 10 g/L; yeast powder: 5 g/L; sodium chloride: 10 g/L; kanamycin: 50 μg/mL.
      b) Cultivation medium (15 liters):
        Disodium hydrogen phosphate: 315 g; potassium dihydrogen phosphate: 100 g; sodium chloride: 10.05 g; ammonium chloride: 50 g; tryptone 90 g.
        The above components were sterilized together in a tank; and the following components were sterilized individually and then added into a fermentation tank.
        Magnesium sulfate: 15 g; glucose: 450 g; feeding (500 g/L): glucose.
      c) Fermentation and induction expression:
        i) Seed culture
          A strain was taken from an identified plate, inoculated in 50 ml LK (250 ml flask), and cultured at 36° C., 200 rmp for 8 hours, and then this 50 ml seed liquid was transferred and inoculated into 700 ml LK and cultured at 36° C., 200 rpm overnight.
        ii) Procedure for fermentation and induction expression
          The cultured seed liquid (OD600=3-4) was added in a tank, the parameters were adjusted as: 36° C., 150 rpm, and dissolved oxygen 100%, and the fermentation was performed; after 5 hours, about 800 ml feeding was fed at a rate of 2.5 for 2 hours, and 1 g of IPTG was added for induction (3 hours).
  3) Chromatography
    (i) Affinity chromatography
      GSH-Agrose chromatographic medium (Pharmacia Inc.) was used, the balanced solution was 25 mM Tris-HCl, pH8, and after loading and balancing, the centrifugal supernatant of lyzed cells was loaded on a Glutathione Sepharose column (Pharmacia Inc.). After balancing, the fusion protein was eluted by an eluant comprising 10 mM reduced glutathione (GSH).
    (ii) Enzymolysis
      The eluant of the above step was enzymatically digested at 37° C. for 2 hours by adding thrombin (5 NIHU/mL).
    (iii) Anion exchange chromatography
      Source30Q chromatographic medium (Pharmacia Inc.) was used, the balanced solution was 20 mM PB (disodium hydrogen phosphate—sodium dihydrogen phosphate), pH7, the sample obtained by enzymolysis in the step (2) was diluted with an equivalent volume of water and loaded, after balancing, desired protein elution peaks were collected by a gradient eluent of 20 mM PB, pH7, 0-1M NaCl.
  4) Detection
    The purity of Gly-Tβ4 obtained by the above purification steps were determined as greater than 98% by SDS-PAGE purity assay and reverse phase HPLC assay.

EXAMPLE 2

Preparation of thymosin β4 derivative Ala-Tβ4

1. Preparation of Recombinant Plasmid pGMTβ4-A
  In accordance with the known amino acid sequence of Tβ4 (SEQ ID NO:1), *E. coli* preferential codon was used for genetic synthesis de novo of Tβ4 DNA sequence to obtain a Ala-Tβ4 nucleic acid sequence; in the meanwhile, to facilitate manipulation of gene recombination, restriction sites BamHI and XhoI were added at sites corresponding to the N-terminal and C-terminal of the polypeptide, and the N-terminal is modified with alanine, Ala, as shown in SEQ ID NO:4,

```
GGA TCC CCT CGA GCT TCT GAC AAA CCC    (SEQ ID NO:4)
BamHI

GAT ATG GCT GAG ATC GAG AAA TTC GAT

AAG TCG AAA CTG AAG AAG ACA GAG ACG

CAA GAG AAA AAT CCA CTG CCT TCC AAA

GAA ACG ATT GAA CAG GAG AAG CAA GCA

GGC GAA TCG TAA CTC GAG;
              XhoI
``` wherein, the restriction sites were underlined.
The corresponding amino acid sequence is as follows:

```
Ala Ser Asp Lys Pro Asp Met Ala Glu    (SEQ ID NO:5)

Ile GLu Lys Phe Asp Lys Ser Lys Leu

Lys Lys Thr Glu Thr Gln Glu Lys Asn

Pro Leu Pro Ser Lys Glu Thr Ile Glu

Gln Glu Lys Gln Ala Gly Glu Ser;
```

According to the known GST amino acid sequence, a leader peptide DNA sequence was genetically synthesized de novo by using *E. coli* preferential codon, and restriction sites EcoRI and BamHI were added at sites corresponding to the N-terminal and C-terminal of the polypeptide, thereby obtaining a leader peptide nucleic acid sequence, as shown in SEQ ID NO:3:
According to conventional methods in the art (see also, "Molecular Cloning: A Laboratory Manual", $2^{nd}$ Edition, Cold Spring Harbor Laboratory Press America, 1992), the above prepared lead peptide, Ala-Tβ4 and screening plasmid pBSK were digested with restriction enzymes EcoRI, XhoI, BamHI, wherein EcoRI and BamHI were used to digest the leader peptide, XhoI and BamHI were used to digest Gly-Tβ4, and EcoRI and XhoI were used to digest the screening plasmid pBSK, wherein after calculation of concentrations of each component, they were added in a molar ratio of 1:1 into a T4 ligation system. After transforming and screening, a recombinant plasmid comprising the gene of said Ala-Tβ4 nucleic acid sequence and the leader peptide fusion protein was obtained and named as pSK-Tβ42.

The said fusion protein gene was digested by corresponding restriction enzymes separately, and then the fusion protein gene fragment and the recovered large fragment of plasmid pGM obtained by double enzyme digestion with XhoI and EcoRI (the plasmid pGM comprising a marker for kanamycin resistance screen, could express GST fusion protein in large quantity, and was constructed by Beijing Northland Biotech Co., Ltd.) were subjected to a connection of three desired gene fragments in a T4 ligase system at 18° C. The obtained recons were identified by digesting and sequencing to obtain a recombinant plasmid with correct linkage, named as pGMT β4-A.

2. Preparation of Genetically Engineered Bacteria Comprising the Recombinant Plasmid Then, *E. coli* BL21 was transformed by $CaCl_2$ method and spread on LB plate containing 50 g/ml kanamycin, and positive colonies were chosen for identifying a transformant containing the said recombinant plasmid pGMTβ4-A. The said transformant was cultured in LK liquid medium until $OD_{600}$ was 0.6-0.8, 0.1 mM IPTG was added for induction of 3-4 hours before the bacteria were collected by centrifugation, then broken with 8M urea. One protein band of about 30 KD in 15% SDS-PAGE electrophoresis was shown with an expression level of 40%. The immunoblot assay of Tβ4 monoclonal antibody exhibited positive reaction. The obtained genetically engineered strain with high expression of thymosin derivative Ala-Tβ4 protein was named as PGMTβ4/BL21.

According to the above preparation method, a genetically engineered strain with high expression of thymosin derivative Ala-Tβ4 obtained by the applicant was named as PGMT β4-A/BL21 (access number of deposit: CGMCC No. 1750).

3. Expression and Purification of Gly-Tβ4

1) Expression in shake flask: the genetically engineered strain PGMT β4-A/BL21 comprising Ala-Tβ4 protein gene as above prepared was cultured overnight in LB medium comprising 50 μg/ml kanamycin (37° C., 200 nm p), then was inoculated in a ratio of 1:30 into a LB medium comprising 50 μg/ml kanamycin, and cultured at 37° C. for 3 hours, then was induced for 4 hours by adding 0.1 mM IPTG Cells were collected and analyzed by SDS-PAGE electrophoresis, and it was found that the thymosin derivative Ala-Tβ4 (30 KD) was mainly in form of soluble expression product, and the quantity of the expression product was 60% based on the total protein.

2) Large Scale Fermentation and Expression
A. Composition of culture media
a) Seed liquid medium (LK):
Tryptone: 10 g/L; yeast powder: 5 g/L; sodium chloride: 10 g/L; kanamycin: 50 μg/mL.
b) Cultivation medium (15 liters):
Disodium hydrogen phosphate: 315 g; potassium dihydrogen phosphate: 10 g; sodium chloride: 10.05 g; ammonium chloride: 50 g; tryptone 90 g.

The above components were sterilized together in a tank; and the following components were sterilized individually and then added into a fermentation tank. Magnesium sulfate: 15 g; glucose: 450 g; feeding (500 g/L): glucose.

c) Fermentation and induction expression:
i) Seed culture
A strain was taken from an identified plate, inoculated in 50 ml LK (250 ml flask), and cultured at 36° C., 200 rmp for 8 hours, and then this 50 ml seed liquid was transferred and inoculated in 700 ml LK and cultured at 36° C., 200 rpm overnight.
ii) Procedure for fermentation and induction expression
The cultured seed liquid (OD600=3-4) was added in a tank, the parameters were adjusted as: 36° C., 150 rpm, and dissolved oxygen 100%, and the fermentation was performed; after 5 hours, about 800 ml feeding was fed at a rate of 2.5 for 2 hours, and 1 g of IPTG was added for induction (3 hours).

3) Chromatography
(i) Affinity chromatography
GSH-Agrose chromatographic medium (Pharmacia Inc.) was used, the balanced solution was 25 mM Tris-HCl, pH8, and after loading and balancing, the centrifugal supernatant of lyzed cells was loaded on a Glutathione Sepharose column (Pharmacia Inc.). After balancing, the fusion protein was eluted by an eluant comprising 10 mM reduced glutathione (GSH).
(ii) Enzymolysis
The eluant of the above step was enzymatically digested at 37° C. for 2 hours by adding thrombin (5 NIHU/mL).
(iii) Anion exchange chromatography
Source30Q chromatographic medium (Pharmacia Inc.) was used, the balanced solution was 20 mM PB, pH7, the sample obtained by enzymolysis in the step (2) was diluted with an equivalent quantity of water and loaded, after balancing, protein elution peaks were collected by a gradient eluent of 20 mM PB, pH7.0-1M NaCl.

4) Detection
The purity of the Ala-Tβ4 obtained by the above purification steps was determined as greater than 98% by SDS-PAGE purity assay and reverse phase HPLC assay.

EXAMPLE 3

Evaluation of Therapeutic Effects of Thymosin β4 Derivatives Gly-Tβ4 and Ala-Tβ4 and Native Thymosin Tβ4 on Treatment of Heart Ischemia in Rat Models 1. Preparation of Ill Animal Models and Test Method For evaluating and comparing the bioactivity of Gly-Tβ4 and Tβ4 in reduction of heart injury and reduction of heart fibrosis, ill animal models of acute myocardial infarction—rat left anterior descending branch coronary artery reperfusion models were established.

Rats were administrated with xylazine 5 mg/kg by intramuscular injection; anesthetized with ketamine 50 mg/kg, and rat anterior chest wall was disinfected with iodine tincture and alcohol; after completely dry, a sterile operation towel was put on, the operative site was exposed, and the operation was conducted under complete aseptic condition. The skin of rat anterior chest wall was incised, and the $3^{rd}$ to the $6^{th}$ ribs were cut to expose thoracic cavity, the lung was pushed aside, the heart vesicle was opened to expose the heart. Blood vessel from the origin of left anterior descending branch coronary artery to 3 mm was ligated with 6-0 polypropylene ligature wire and NELATION, and the reperfusion was conducted 1 hour later. After non-hemorrhage was confirmed, the excised ribs were sutured with sternum, and then skin was sutured. After operation, the rats were administrated with 3 mg/kg/day gentamicin for 3 days by intramuscular injection for prevention of infection.

2. Comparison of Thickness of Anterior Left Ventricular Wall by Using Ultrasonic Cardiogram 1) Comparison between Gly-Tβ4 and Tβ4

After the rat heart ischemia models were established according to the step 1, negative control group (20 rats, injection with physiological saline 200 μl/rat/day), positive control group (20 rats, intra-peritoneal injection with native thymosin Tβ4 10 μg/rat/day), and test group (20 rats, intra-peritoneal injection with thymosin Gly-Tβ4 10 μg/rat/day) were administrated, respectively.

The thickness of anterior left ventricular wall of animals in these groups were measured at the $14^{th}$, $28^{th}$ and $56^{th}$ day after administration by using ultrasonic cardiogram (Live 3D Echo 7500) and probe (15-16L). The results were as follows:

As for basal value (the $0^{th}$ day, before administration), the negative control group was of 0.2682±0.01, the positive control group was of 0.251310.032, the Gly-Tβ4 group was of 0.2499±0.0225, and no significant difference existed between groups. On the $14^{th}$ day after administration, the negative control group was of 0.1365±0.0125, the positive control group was of 0.1919±0.012, and there was a significant difference ($p=0.048<0.05$) between the negative control group and the positive control group. The Gly-Tβ4 group was of 0.2162±0.0078, and there was a significant difference ($p=0.086<0.1$) between groups.

Figure 1:
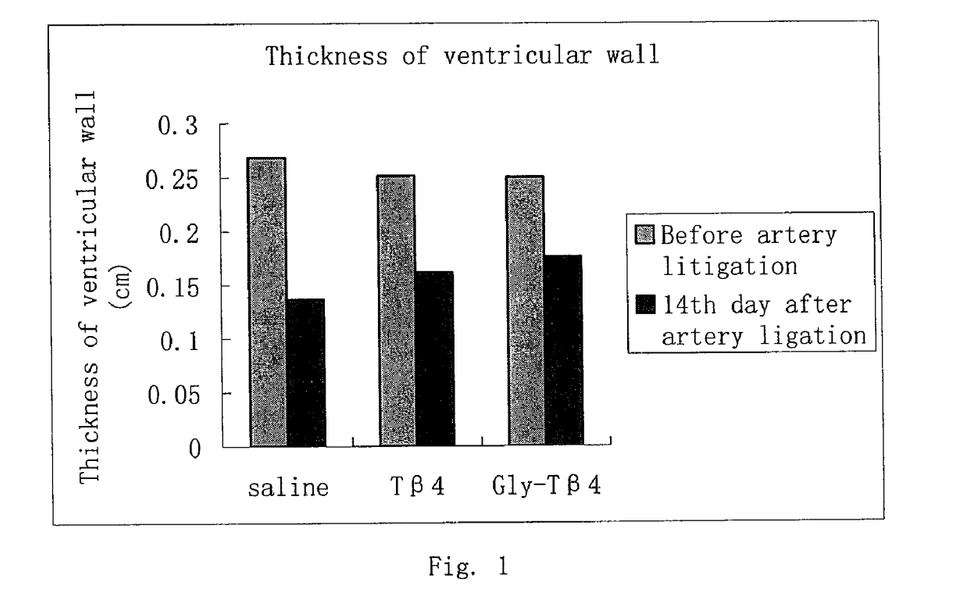
FIG. 1 illustrates the effects of the injection of Tβ4 and Gly-Tβ4 on the thickness of rat heart wall in rat models.

These results showed that Gly-Tβ4 and Tβ4 both could recover the reduction of thickness of anterior left ventricular wall caused by myocardial infarction (see FIG. 1), wherein the effects of the said Gly-Tβ4 for increasing thickness of anterior left ventricular wall were surprisingly better than the effects of Tβ4.

2) Comparison between Ala-Tβ4 and Tβ4

After the rat heart ischemia models were established according to the step 1, negative control group (20 rats, injection with physiological saline 200 μl/rat/day), positive control group (20 rats, intraperitoneal injection with native thymosin Tβ4 10 μg/rat/day), and test group (20 rats, intraperitoneal injection with thymosin Ala-Tβ4 10 μg/rat/day) were administrated, respectively.

The thickness of anterior left ventricular wall of animals in these groups were measured at the $14^{th}$, $28^{th}$ and $56^{th}$ day after administration by using ultrasonic cardiogram (Live 3D Echo 7500) and probe (15-16L). The results were as follows:

As for basal value (the $0^{th}$ day, before administration), the negative control group was of 0.2594±0.0225, the positive control group was of 0.2378±0.018, the Ala-Tβ4 group was of 0.2432±0.01, and no significant difference existed between groups.

On the $14^{th}$ day after administration, the negative control group was of 0.1306±0.0128, the positive control group was of 0.1215±0.013, the Ala-Tβ4 group was of 0.1299±0.011, and there was no significant difference between groups.

On the $28^{th}$ day after administration, the negative control group was of 0.1207±0.0151, the positive control group was of 0.1233±0.0071, the Ala-Tβ4 group was of 0.1288±0.012, and there was no significant difference between groups.

On the $56^{th}$ day after administration, the negative control group was of 0.1288±0.012, the positive control group was of 0.1232±0.0057, the Ala-Tβ4 group was of 0.1672±0.0078, and thus the increase of thickness of anterior left ventricular wall of the Ala-Tβ4 group was signification ($p<0.05$).

Figure 5:
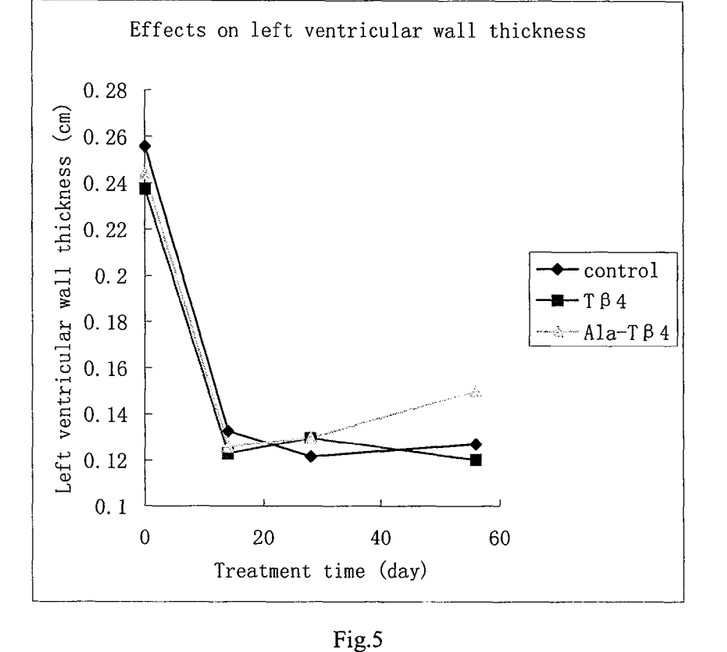
FIG. 5 illustrates the effects of the injection of Tβ4 and Ala-Tβ4 on the thickness of rat heart wall in rat models.

These results showed that Ala-Tβ4 could effectively recover the reduction of thickness of anterior left ventricular wall caused by myocardial infarction (see FIG. 5), wherein the effects of the said Ala-Tβ4 for increasing thickness of anterior left ventricular wall were surprisingly better than the effects of Tβ4.

3. Comparison of Degree of Heart Ventricle Fibrosis by Using Histological Pictures After the rat heart ischemia models were established according to the step 1, negative control group (20 rats, injection with physiological saline 200 μl/rat/day), positive control group (20 rats, intraperitoneal injection with native thymosin Tβ4 10 μg/rat/day), and test group (20 rats, intraperitoneal injection with thymosin Gly-Tβ4 10 μg/rat/day) were administrated, respectively. The results are as follows.

On the $56^{th}$ day after the administration, rat hearts were taken out and were cross cut based on papillary muscle to form sections. The sections were socked in 1% formaldehyde, then processed to make paraffin tissue sections and glass slides, and stained with Masson' trichrome. The comparison between groups was performed by using Image-pro®PLUS ver.4.1 (Media Cybernetics).

1) Comparison Between Gly-Tβ4 and Tβ4

The ratio of fibrosis part of myocardium based on total myocardium of left ventricle was as follows: the negative control group=30.02±5.1%, the positive control group 23.15±2.9% ($P<0.05$), and the Gly-Tβ4 group=15.36±2.7% ($P<0.0005$).

Figure 2:
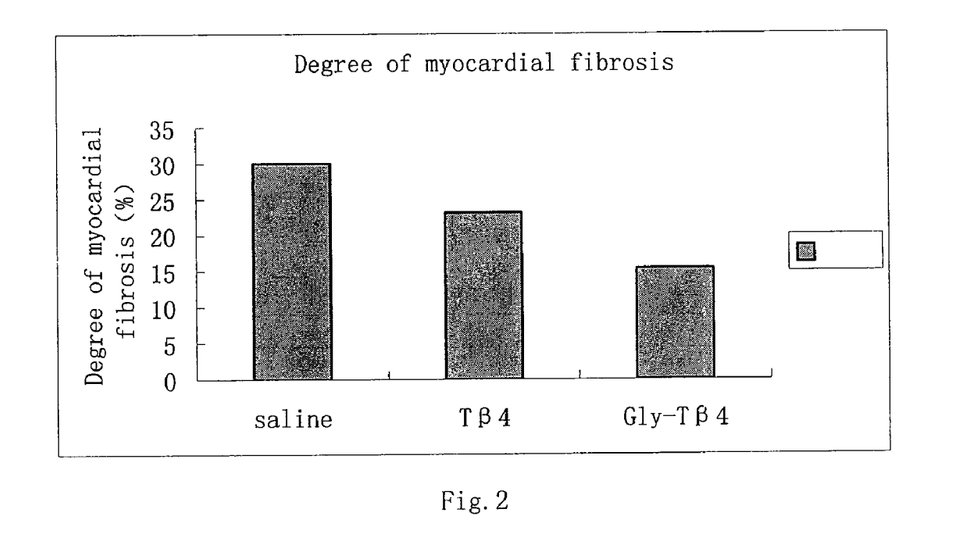
FIG. 2 illustrates the effects of the injection of Tβ4 and Gly-Tβ4 on the fibrosis of rat heart wall in rat models.

The above results showed that the positive control group and the Gly-Tβ4 group exhibited significant difference in comparison with the negative control group, especially the Gly-Tβ4 group exhibited very significant difference. These results indicated that both Gly-Tβ4 and Tβ4 could effectively reduce the fibrosis of myocardium caused by myocardial infarction (see FIG. 2), wherein the effects of Gly-Tβ4 for reducing myocardial fibrosis were surprisingly better than that of Tβ4.

2) Comparison Between Ala-Tβ4 and Tβ4

Figure 6:
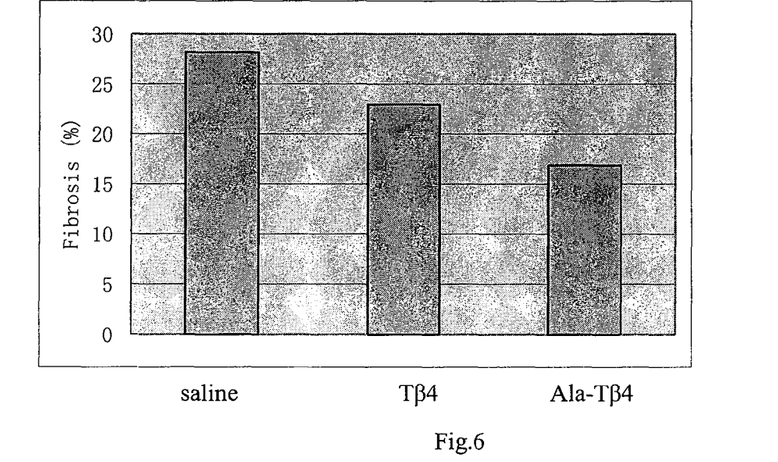
FIG. 6 illustrates the effects of the injection of Tβ4 and Ala-Tβ4 on the fibrosis of rat heart wall in rat models.

The ratio of fibrosis part of myocardium based on total myocardium of left ventricle was as follows: the negative control group=28.13±2.1%, the positive control group 22.91±2.3% ($P<0.05$), and the Ala-Tβ4 group=16.86±1.8% ($P<0.0005$). The above results showed that the positive control group and the Ala-Tβ4 group exhibited significant difference in comparison with the negative control group, especially the Ala-Tβ4 group exhibited very significant difference. These results indicated that both Ala-Tβ4 and Tβ4 could effectively reduce the fibrosis of myocardium caused by myocardial infarction (see FIG. 6), wherein the effects of Ala-Tβ4 for reducing myocardial fibrosis were surprisingly better than that of Tβ4.

EXAMPLE 4

Evaluation of Therapeutic Effects of Gly-Tβ4, Ala-Tβ4 and Tβ4 in Treatment of Epidermis Lesion in Rat Model 1. Preparation of in Animal Models and Test Method For evaluating and comparing the activity of Gly-Tβ4 and Tβ4 for repairing epidermal tissue injury, epidermis lesion ill animal models—rat epidermis lesion models were established.

Rats were administrated with xylazine 5 mg/kg by intramuscular injection; anesthetized with ketamine 50 mg/kg, and rat posterior skin was disinfected with iodine tincture and alcohol; after completely dry, a sterile operation towel was put on, the operative site was exposed, and the operation was conducted under complete aseptic condition. The rat posterior skin was incised to form 3 cm incision.

2. Measurement of Wound Length by Using Computer Image Analysis System

1) Comparison Between Gly-Tβ4 and Tβ4

After rat epidermis lesion models were established according to the step 1, negative control group (10 rats, physiological saline 50 μl/rat/day), positive control group (10 rats, native thymosin 5 μg/50 μl/day), and test group (20 rats, thymosin derivative Gly-Tβ4 5 μg/5 μl/day) were administrated by smearing them on epidermis, 4 times per day.

On the $5^{th}$ day, wound lengths were measured by using a computer image analysis system. The results were as follows:

As for basal value (the $0^{th}$ day, before administration), the negative control group was of 3.13±0.21, the positive control group was of 3.07±0.18, the Gly-Tβ4 group was of 3.13±0.11, and no significant difference existed between groups.

On the $5^{th}$ day, the negative control group was of 2.37±0.18, the positive control group was of 1.62±0.13, the Gly-Tβ4 group was of 1.14±0.12, and significant difference existed between groups.

Figure 3:
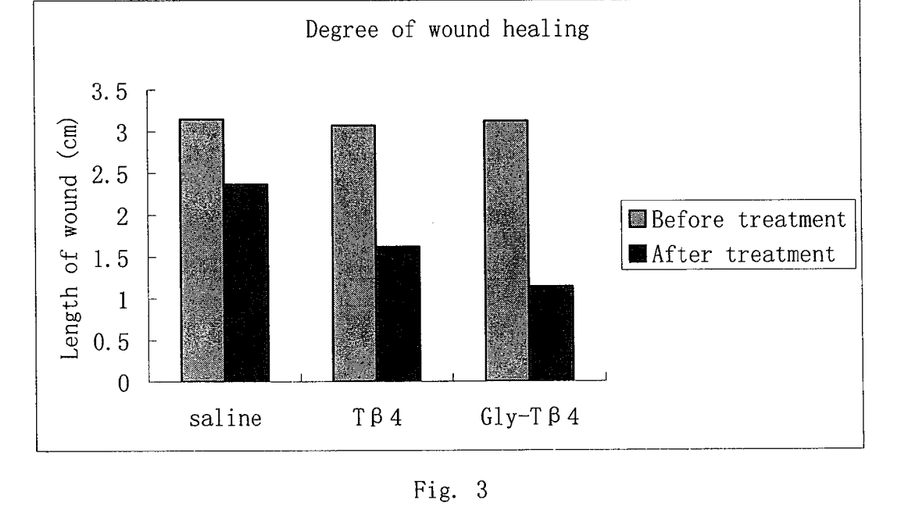
FIG. 3 illustrates the effects of the administration of Tβ4 and Gly-Tβ4 on the healing of the injured epidermis of rats in rat models.

These results showed that Gly-Tβ4 could effective promote the healing of epidermis wounds (see FIG. 3), wherein the activity of Gly-Tβ4 for promoting the healing of epidermis wounds was surprisingly stronger than that of Tβ4.

2) Comparison Between Ala-Tβ4 and Tβ4

After rat epidermis lesion models were established according to the step 1, negative control substance (PBS), positive control substance (GT1β4) and test substance group (Ala-Tβ4) were administrated topically by nebulizer, 4 times per day. The drug concentration of Tβ4 and Ala-Tβ4 were 100 μg/ml. The healing of wounds were observed everyday after administration.

Test Results:

(1) Wound inflammatory reaction: the wounds of the PBS group had obvious inflammatory reactions such as red swelling, exudation, etc., which persisted for about 2-3 days; the Tβ4 group and the Ala-Tβ4 group had relatively slight inflammatory reactions, which persisted for about 1-2 days.

Figure 7:
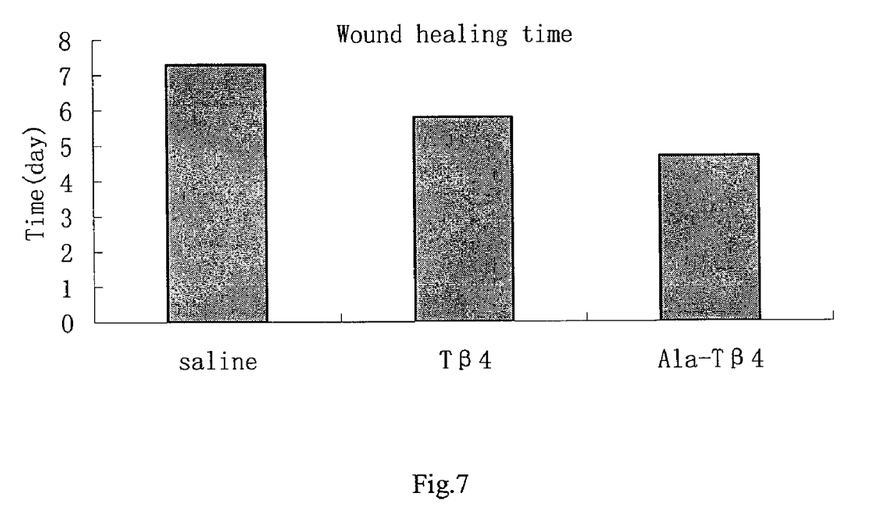
FIG. 7 illustrates the effects of the administration of Tβ4 and Ala-Tβ4 on the healing time of the epidermal wound of rats in rat models.

(2) Wound healing time: the PBS group was of 7.3±1.02 days, the Tβ4 group was of 5.8±0.91 days, and the Ala-Tβ4 group was of 4.7±0.83 days. By comparing these groups, the Tβ4 group and the Ala-Tβ4 group had relatively shorter wound healing time than the PBS group ($P<0.05$). The results were shown in FIG. 7.

These results showed that Tβ4 and Ala-Tβ4 could significantly promote the healing of wounds, wherein the wound healing time of the administration of Ala-Tβ4 was obviously shorter than the administration of Tβ4.

(3) Scar size: two weeks after administration, these groups were compared between each other in term of scar size, and the results were that: the negative control scar group was of 2.3±0.31 cm, the Tβ4 group was of 1.9±0.23 cm, and the Ala-Tβ4 group was of 1.7±0.30 cm; and the scars of the Tβ4 group and the Ala-Tβ4 group were relatively fine linear scars with relatively smooth surface, while the scars of the negative control group were relatively thick scars with non-smooth surface.

Figure 8:
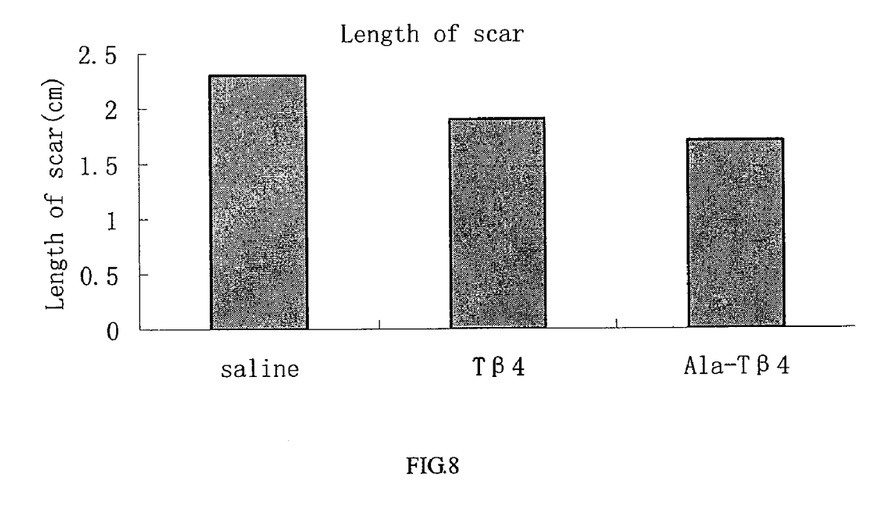
FIG. 8 illustrates the effects of the administration of Tβ4 and Ala-Tβ4 on the degree of scar of the epidermal wound of rats in rat models.

By comparing these groups, the wound scars of the Tβ4 group and the Ala-Tβ4 group were obviously smaller than that of the PBS group ($P<0.05$). The results were shown in FIG. 8.

The results showed that both Tβ4 and Ala-Tβ4 had significant function against scarring, wherein the wound scars size when Ala-Tβ4 was administrated were significantly smaller than that when Tβ4 was administrated.

EXAMPLE 5

Evaluation of Therapeutic Effects of Gly-Tβ4, Ala-Tβ4 and Tβ4 in Treatment of Corneal Lesion in Rat Models 1. Comparison between Gly-Tβ4 and Tβ4

(1) Preparation of Ill Animal Models and Test Method

For evaluating the activity of Gly-Tβ4 and Tβ4 for repairing corneal tissue injury, the ill animal models of acute corneal lesion—rat cornea alkali burn models were established.

Filter paper pieces with a diameter of 2 mm were soaked in 1N caustic soda, then the soaked filter paper pieces were placed exactly at the centers of rat corneas, and after 30 seconds, the rat corneas were washed with PBS sufficiently, and treated immediately with Gly-Tβ4 and Tβ4. After 4 days, eyeballs were exenterated, fixed with 10% formaldehyde, embedded with paraffin and continuously sectioned along pupil optic nerve plane, the obtained sections were used for collection and analysis of recovery of corneal epithelium by image analysis system.

(2) Measurement of Recovery of Corneal Epithelium by Using Computer Image Analysis System After the rat corneal lesion models were established according to the step 1, negative control group (10 rats, topically administrated with eyedrops, physiological saline 30111/rat, 4 times per day), positive control group (10 rats, native thymosin 30 μl/rat, 4 times per day), and test group (10 rats, thymosin Gly-Tβ4 30 μl/rat, 4 times per day) were administration ocularly.

After 4 days of administration, eyeballs were exenterated, fixed with 10% formaldehyde and embedded with paraffin, and continuously sectioned along pupil optic nerve plane, the obtained sections were used for collection and analysis of recovery of corneal epithelium by image analysis system. The results were as follows.

Basal value (on the $0^{th}$ day, before administration), the negative control group was of 4.82±0.12, the Tβ4 group was of 4.76±0.18, the Gly-Tβ4 group was of 4.85±0.16, and no significant difference existed between groups.

On the 4th day after administration, the negative control group was of 4.89±0.12, the Tβ4 group was of 7.03±0.13, the Gly-Tβ4 group was of 7.621±0.11, so the Tβ4 group and the Gly-Tβ4 group were significantly different from the negative control group, especially, the Gly-Tβ4 group was very significantly different from the negative control group.

Figure 4:
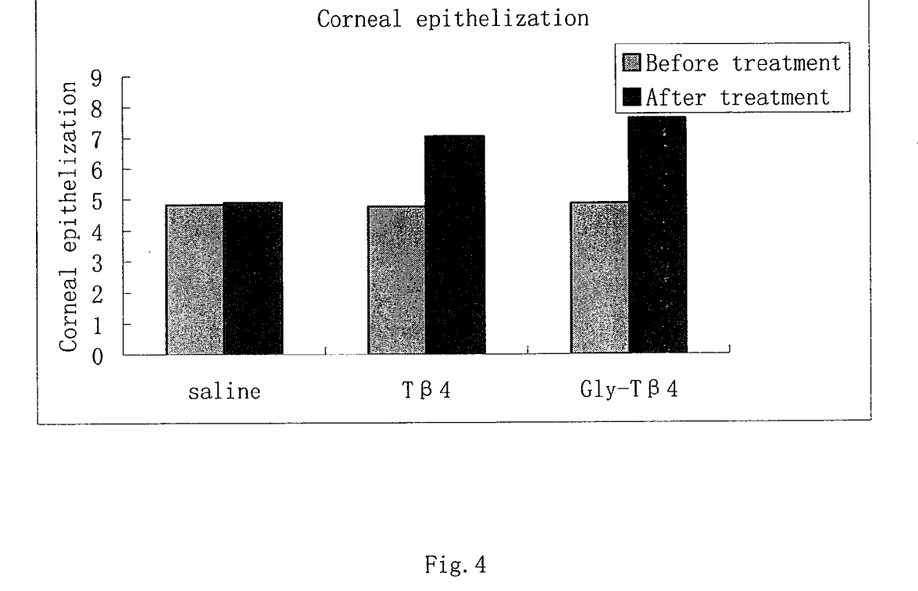
FIG. 4 illustrates the effects of the administration of Tβ4 and Gly-Tβ4 on the epidermization of the injured cornea of rats in rat models.

These results showed that both Tβ4 and Gly-Tβ4 could effectively promote the recovery of alkali-burned cornea (see FIG. 4), wherein the activity of Gly-Tβ4 for promoting the repair of corneal lesion was surprisingly better than that of Tβ4.

2. Comparison between Ala-Tβ4 and Tβ4

(1) Preparation of Ill Animal Models and Test Method

For evaluating the effectiveness of Ala-Tβ4 and Tβ4, the ill animal models of acute corneal lesion—rabbit cornea alkali burn models were established.

Filter paper pieces with a diameter of 8 mm were soaked in 1N caustic soda, then the soaked filter paper pieces were placed exactly at the centers of rabbit corneas, and after 30 seconds, the rabbit corneas were washed with physiological saline sufficiently, and treated immediately with Ala-Tβ4 and Tβ4. Eyeballs were exenterated separately after 1 and 5 days, fixed with 10% formaldehyde, embedded with paraffin, and continuously sectioned along pupil optic nerve plane, the obtained sections were stained and used for collection and analysis of recovery of corneal epithelium by image analysis system.

(2) Administration Protocol

After the rabbit cornea alkali burn models were established, negative control substance (PBS), positive control substance (Tβ4), and test substance (Ala-Tβ4) were administrated topically with eyedrops, 4 times per day. The drug concentration of Tβ4 and Ala-Tβ4 were 500 μg/ml, and the recovery of cornea was observed everyday after administration.

(3) Test Results

Figure 9A:
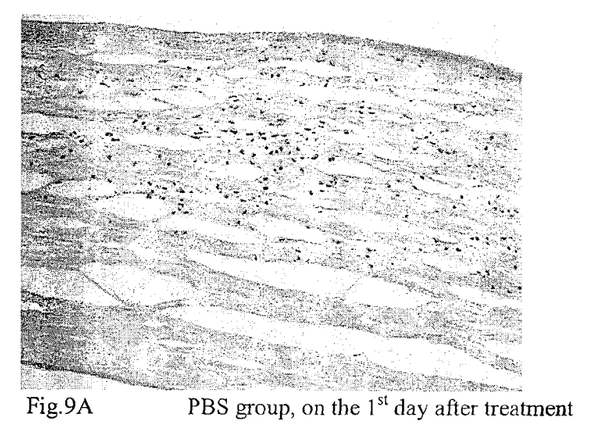
FIGS. 9A-C illustrates the observation results of alkali burn of corneal epithelium on day 1 after administration of Tβ4 group (9C), Ala-Tβ4 group (9B) and PBS group (9A) in rabbit cornea alkali burn models.
Figure 9B:
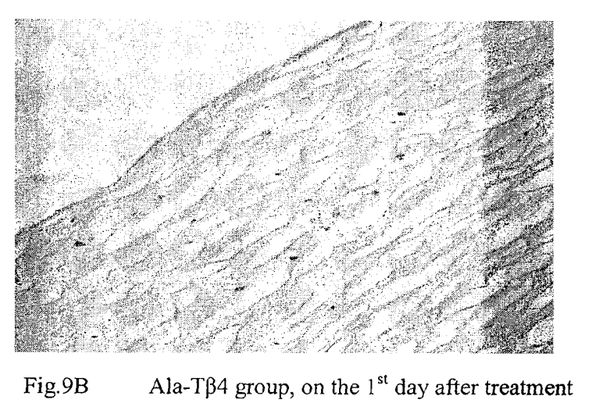
Figure 9C:
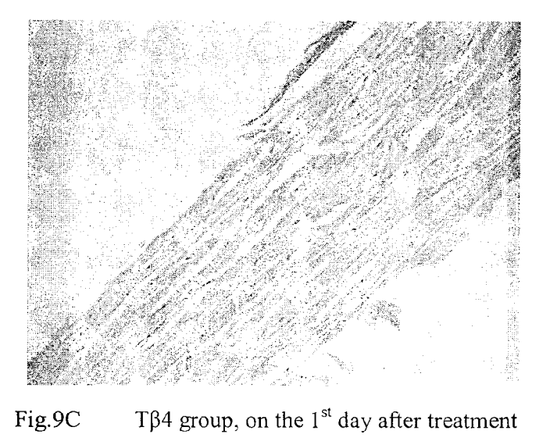
Figure 10A:
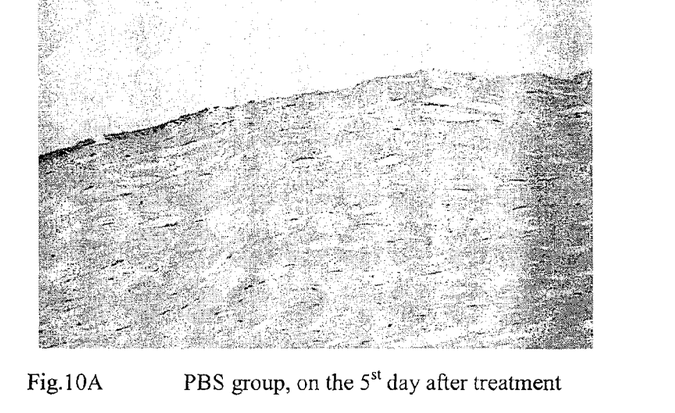
FIGS. 10A-C illustrates the observation results of recovery of the alkali burn of corneal epithelium on day 5 after administration of Tβ4 group (10C), Ala-Tβ4 group (10B) and PBS group (10A) in rabbit cornea alkali burn models.
Figure 10B:
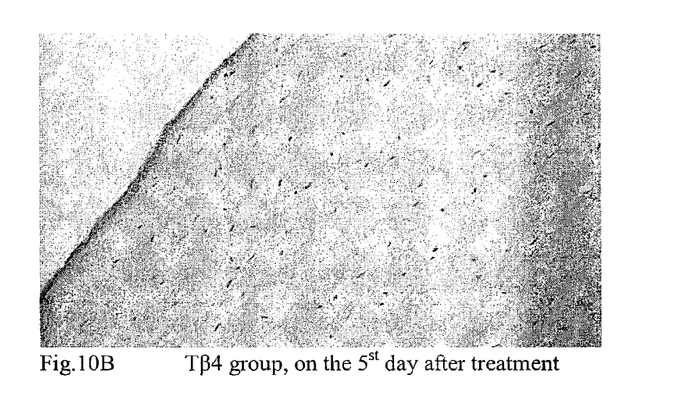
Figure 10C:
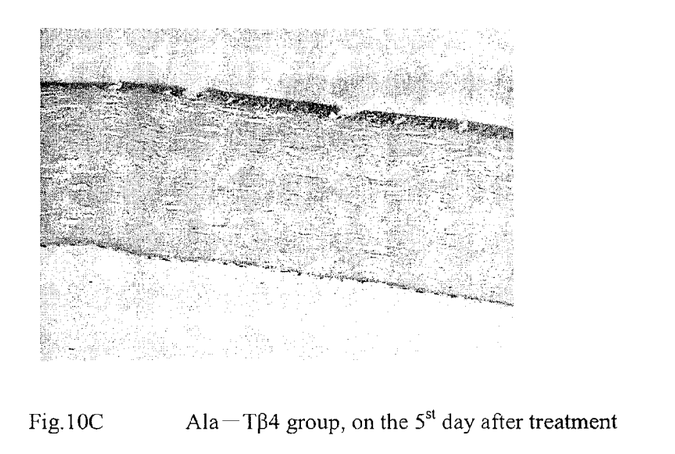

Recovery condition of corneal epithelium: on the 1st day, alkali burned corneal epitheliums were observed in all the Tβ4 group, the Ala-Tβ4 group and the PBS group (see FIG. 9A-C). However, on the 5th day when the test was completed, it was found in the PBS group that some corneal epithelial cells did not grow up (see FIG. 10A); on the 5th day when the test was completed, it was found in the Tβ4 group that all injured corneal epithelial cells were recovered and became normal, and 1-2 layers of epithelial cells appeared (see FIG. 10B); on the 5th day when the test was completed, it was found in the Ala-Tβ4 group that all injured corneal epithelial cells were recovered and became normal, and 3-4 layers of epithelial cells appeared (see FIG. 10C). By comparing these groups, the recovery of corneal epithelium in the Tβ4 group and the Ala-Tβ4 group was obviously better than that in the PBS group, and the recovery of corneal epithelium in the Ala-Tβ4 group was obviously better than that in the Tβ4 group. The results indicated that Tβ4 and Ala-Tβ4 both had significant function for promoting the recovery of alkali burned corneal epithelium, wherein the Ala-Tβ4 had better function than Tβ4.

What is claimed is:

1. An isolated thymosin β4 derivative, which is Gly-Tβ4 consisting of the amino acid sequence of SEQ ID NO: 6.

2. A pharmaceutical composition, comprising a thymosin β4 derivative according to claim 1, and optionally a pharmaceutically acceptable carrier.

3. A method for treatment of skin lesion, heart injury, corneal lesion and/or coronary heart disease, comprising applying an effective amount of the thymosin β4 derivative according to claim 1 to a subject.

4. The method according to claim 3, wherein said subject is a human being.

* * * * *

UNITED STATES PATENT AND TRADEMARK OFFICE
CERTIFICATE OF CORRECTION

| | |
|---|---|
| PATENT NO. | : 7,816,321 B2 |
| APPLICATION NO. | : 11/995817 |
| DATED | : October 19, 2010 |
| INVENTOR(S) | : Liya Nie et al. |

Page 1 of 1

It is certified that error appears in the above-identified patent and that said Letters Patent is hereby corrected as shown below:

Item 73
"Beijing Northland Biotech. Co., Ltd., Beijing (CN)" should read, --Beijing Northland Biotech. Co., Ltd., Beijing (CN); Biotoxtech Co., Ltd., Chungcheongbuk-Do (KR)--.

Signed and Sealed this
Ninth Day of October, 2012

David J. Kappos
*Director of the United States Patent and Trademark Office*

SEQUENCE LISTING

<160> NUMBER OF SEQ ID NOS: 6

<210> SEQ ID NO 1
<211> LENGTH: 43
<212> TYPE: PRT
<213> ORGANISM: Homo sapiens

<400> SEQUENCE: 1

Ser Asp Lys Pro Asp Met Ala Glu Ile Glu Lys Phe Asp Lys Ser Lys
1               5                   10                  15

Leu Lys Lys Thr Glu Thr Gln Glu Lys Asn Pro Leu Pro Ser Lys Glu
            20                  25                  30

Thr Ile Glu Gln Glu Lys Gln Ala Gly Glu Ser
        35                  40

<210> SEQ ID NO 2
<211> LENGTH: 141
<212> TYPE: DNA
<213> ORGANISM: Artificial
<220> FEATURE:
<223> OTHER INFORMATION: Synthesized sequence Gly-T-beta 4

<400> SEQUENCE: 2
ggatccgaca aacccgatat ggctgagatc gagaaattcg ataagtcgaa actgaagaag     60
acagagacgc aagagaaaaa tccactgcct tccaaagaaa cgattgaaca ggagaagcaa    120
gcaggcgaat cgtaactcga g                                              141

-continued

```
<210> SEQ ID NO 3
<211> LENGTH: 684
<212> TYPE: DNA
<213> ORGANISM: artificial
<220> FEATURE:
<223> OTHER INFORMATION: Synthesized sequence CST

<400> SEQUENCE: 3
gaattcatgt cccctatact aggttattgg aaaattaagg gccttgtgca acccactcga      60
cttcttttgg aatatcttga agaaaaatat gaagagcatt tgtatgagcg cgatgaaggt     120
gataaatggc gaaacaaaaa gtttgaattg ggtttggagt ttcccaatct tccttattat     180
attgatggtg atgttaaatt aacacagtct atggccatca tacgttatat agctgacaag     240
cacaacatgt tgggtggttg tccaaaagag cgtgcagaga tttcaatgct tgaaggagcg     300
gttttggata ttagatacgg tgtttcgaga attgcatata gtaaagactt tgaaactctc     360
aaagttgatt ttcttagcaa gctacctgaa atgctgaaaa tgttcgaaga tcgtttatgt     420
cataaaacat atttaaatgg tgatcatgta acccatcctg acttcatgtt gtatgacgct     480
cttgatgttg ttttatacat ggacccaatg tgcctggatg cgttcccaaa attagtttgt     540
tttaaaaaac gtattgaagc tatcccacaa attgataagt acttgaaatc cagcaagtat     600
atagcatggc ctttgcaggg ctggcaagcc acgtttggtg gtggcgacca tcctccaaaa     660
tcggatctgg ttccgcgtgg atcc                                             684

<210> SEQ ID NO 4
<211> LENGTH: 153
<212> TYPE: DNA
<213> ORGANISM: artificial
<220> FEATURE:
<223> OTHER INFORMATION: Synthesized sequence Ala-T-beta4

<400> SEQUENCE: 4 ggatccccctc gagcttctga caaacccgat atggctgaga tcgagaaatt cgataagtcg      60
aaactgaaga agacagagac gcaagagaaa aatccactgc cttccaaaga aacgattgaa     120
caggagaagc aagcaggcga atcgtaactc gag                                   153

<210> SEQ ID NO 5
<211> LENGTH: 44
<212> TYPE: PRT
<213> ORGANISM: artificial
<220> FEATURE:
<223> OTHER INFORMATION: Synthesized sequence Ala-T-beta 4

<400> SEQUENCE: 5

Ala Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40

<210> SEQ ID NO 6
<211> LENGTH: 44
<212> TYPE: PRT
<213> ORGANISM: artificial
<220> FEATURE:
<223> OTHER INFORMATION: Synthesized sequence Gly-T-beta 4
```

```
-continued

<400> SEQUENCE: 6

Gly Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
            35                  40
```